(12) United States Patent
Yelken

(10) Patent No.: US 10,834,978 B1
(45) Date of Patent: Nov. 17, 2020

(54) SOFT SILICONE EDGED CUSHION FOR FACE MASKS

(71) Applicant: Suat Yelken, Baltimore, MD (US)

(72) Inventor: Suat Yelken, Baltimore, MD (US)

(*) Notice: Subject to any disclaimer, the term of this patent is extended or adjusted under 35 U.S.C. 154(b) by 0 days.

(21) Appl. No.: 16/993,578

(22) Filed: Aug. 14, 2020

Related U.S. Application Data

(63) Continuation of application No. 16/880,496, filed on May 21, 2020.

(60) Provisional application No. 63/027,287, filed on May 19, 2020.

(51) Int. Cl.
- *A41D 13/11* (2006.01)
- *A41D 13/015* (2006.01)
- *A41D 13/00* (2006.01)

(52) U.S. Cl.
CPC ............ *A41D 13/015* (2013.01); *A41D 13/11* (2013.01)

(58) Field of Classification Search
CPC .......... A61M 16/0683; A61M 16/0616; A61M 16/0605; A61M 16/0622; A61M 16/0688; A61M 2205/0216; A61M 2210/0618; A61M 2209/08; A61M 2205/0266; G02C 11/12; G02C 3/003; G02C 2200/08; G02C 5/12; G02C 11/02; A62B 23/025; A62B 18/08; A62B 18/084; A62B 18/00; A62B 18/02; A62B 23/00; A62B 23/02; A41D 13/015; A41D 13/11; A41D 13/1176; A41D 13/1138; A41D 13/1161; A41D 13/1169; A41D 13/1192; A41D 13/0556; A41D 13/1107; A61F 9/026; A61F 13/126; A61F 9/045; A61F 2006/042; A61F 2013/00476; A61F 2013/00578; A61F 2013/15024; A61F 2/7812; A42B 3/288; A63B 71/10; F16F 9/306

See application file for complete search history.

(56) References Cited

U.S. PATENT DOCUMENTS

| | | | | |
|---|---|---|---|---|
| 1,853,872 A | * | 4/1932 | Meyrowitz | A61F 9/026 2/440 |
| 2,032,843 A | * | 3/1936 | Grier | G02C 5/126 351/82 |
| 2,612,076 A | * | 9/1952 | Dietz | G02C 5/124 351/55 |

(Continued)

OTHER PUBLICATIONS

Trafton, Anne, "Engineers Design a Reusable, Silicone Rubber Face Mask with an N95 Filter", SciTechDaily, Jul. 12, 2020.

*Primary Examiner* — Robert H Muromoto, Jr.
(74) *Attorney, Agent, or Firm* — Cameron LLP

(57) ABSTRACT

A soft medical silicone edged cushion may significantly reduce air leakage and provide comfort to a wearer of a face mask, for example, when the face mask is continually worn by a healthcare worker for a twelve hour shift of medical duty. The cushion may preferably be U-shaped and comprise a cross-section for holding an extra soft silicone gel, yet be sufficiently hard and elastic and of predetermined circumference to be adaptable to self-installation to the lateral edges of a face mask and coatable to protect from the escape of air and to fit comfortably despite the use of elastic straps with the face mask or the presence of solid plastic lateral edges of an oxygen mask or a ventilator mask. The cushion may be used to cushion a solid plastic laterally edged oxygen or ventilator mask against the use of elastic ties to tie the face mask around a patient's head.

6 Claims, 11 Drawing Sheets

(56) References Cited

U.S. PATENT DOCUMENTS

| | | | | |
|---|---|---|---|---|
| 2,918,676 | A * | 12/1959 | Matheson | A61F 9/026 2/440 |
| 3,548,420 | A * | 12/1970 | Spence | A61F 2/7812 623/37 |
| 3,858,379 | A * | 1/1975 | Graves | A47C 27/085 53/431 |
| 3,939,123 | A * | 2/1976 | Matthews | A61L 15/60 528/60 |
| 4,456,642 | A * | 6/1984 | Burgdorfer | A61G 7/05738 428/68 |
| 4,516,571 | A * | 5/1985 | Buchan | A61F 13/023 128/893 |
| 4,688,562 | A * | 8/1987 | Buchan | A61F 13/00046 128/889 |
| 4,738,257 | A * | 4/1988 | Meyer | A61L 15/58 602/48 |
| 4,856,118 | A * | 8/1989 | Sapiejewski | A61F 11/14 2/209 |
| 4,902,119 | A * | 2/1990 | Porsche | G02C 5/122 351/136 |
| 4,910,060 | A * | 3/1990 | Nakanishi | B29C 65/02 428/447 |
| 4,950,066 | A * | 8/1990 | Hartman | G02C 11/02 351/106 |
| 5,138,722 | A * | 8/1992 | Urella | A61F 11/14 2/209 |
| 5,243,971 | A * | 9/1993 | Sullivan | A61M 16/06 128/204.18 |
| 5,252,373 | A * | 10/1993 | Ganske | B32B 27/08 428/68 |
| 5,320,112 | A * | 6/1994 | Bloodsaw | A61F 6/04 128/842 |
| 5,362,834 | A * | 11/1994 | Schapel | C08G 18/4816 528/58 |
| 5,467,765 | A * | 11/1995 | Maturaporn | A41D 13/1115 128/206.12 |
| 5,590,430 | A * | 1/1997 | Sereboff | A47C 27/086 5/655.5 |
| 5,608,469 | A * | 3/1997 | Boll | A61F 9/029 2/449 |
| 5,711,026 | A * | 1/1998 | Kaltman | A61F 13/126 128/858 |
| D391,575 | S * | 3/1998 | Bergin | D14/223 |
| 5,748,278 | A * | 5/1998 | Simmons, Sr. | A61F 9/045 2/449 |
| 5,790,230 | A * | 8/1998 | Sved | A61F 9/025 351/110 |
| 5,828,438 | A * | 10/1998 | Kuo-Tseng | G02C 5/12 351/137 |
| 5,883,026 | A * | 3/1999 | Reader | D04H 1/559 442/382 |
| 5,885,675 | A * | 3/1999 | Martin | G02C 5/00 156/242 |
| 6,062,688 | A * | 5/2000 | Vinas | A61F 9/025 351/44 |
| 6,106,117 | A * | 8/2000 | Huang Lin | G02C 5/122 351/136 |
| 6,119,693 | A * | 9/2000 | Kwok | A61M 16/06 128/201.11 |
| 6,163,615 | A * | 12/2000 | Callahan | H04R 1/1008 381/371 |
| D444,491 | S * | 7/2001 | Iwanaga | D16/333 |
| 6,513,171 | B1 * | 2/2003 | Soper | A61F 9/026 2/436 |
| D473,582 | S * | 4/2003 | Gardner | D16/300 |
| 7,117,543 | B1 * | 10/2006 | Gunnarshaug | A61F 13/126 2/206 |
| 7,425,065 | B2 * | 9/2008 | Wang | G02C 5/126 351/137 |
| 7,827,990 | B1 * | 11/2010 | Melidis | A61M 16/0605 128/206.24 |
| D651,641 | S * | 1/2012 | Fulton | D16/333 |
| 8,235,045 | B2 * | 8/2012 | Moore | A61M 16/0633 128/206.24 |
| 8,303,110 | B1 * | 11/2012 | Weaver | G02C 11/10 351/82 |
| 8,371,302 | B2 * | 2/2013 | Ging | A61M 16/0057 128/206.24 |
| 8,555,413 | B2 * | 10/2013 | Beliveau | A61F 9/029 2/9 |
| 8,820,327 | B2 * | 9/2014 | Melidis | A61M 16/06 128/206.24 |
| 9,004,680 | B2 * | 4/2015 | Havens-Olmstead | G02C 5/126 351/125 |
| 9,192,521 | B2 * | 11/2015 | Boothman | A61F 13/022 |
| 9,963,611 | B2 * | 5/2018 | Stewart | A61P 31/04 |
| 10,018,852 | B2 * | 7/2018 | Hamilton | G02C 5/124 |
| 10,071,216 | B2 * | 9/2018 | Rutan | A62B 18/08 |
| 10,113,043 | B2 * | 10/2018 | Peterson | C08J 9/405 |
| 10,133,305 | B1 * | 11/2018 | Sullivan | G06F 1/1637 |
| 10,627,652 | B2 * | 4/2020 | Froissard | G02C 13/001 |
| 2003/0123022 | A1 * | 7/2003 | Mulvey | G02C 3/003 351/103 |
| 2004/0000313 | A1 * | 1/2004 | Gaynor | B01D 39/1623 128/205.27 |
| 2004/0244799 | A1 * | 12/2004 | Landis | A61M 16/0683 128/206.21 |
| 2004/0255946 | A1 * | 12/2004 | Gerson | A41D 13/1138 128/205.27 |
| 2005/0199239 | A1 * | 9/2005 | Lang | A61M 16/0616 128/206.24 |
| 2005/0279367 | A1 * | 12/2005 | Klemperer | A61M 16/0694 128/861 |
| 2006/0081251 | A1 * | 4/2006 | Hernandez | A61M 16/06 128/206.21 |
| 2006/0107431 | A1 * | 5/2006 | Curran | A61F 9/068 2/7 |
| 2006/0107960 | A1 * | 5/2006 | Smart | A61M 16/0825 128/206.24 |
| 2006/0130845 | A1 * | 6/2006 | Schegerin | A62B 18/08 128/206.28 |
| 2006/0198903 | A1 * | 9/2006 | Storey | C23C 14/0021 424/618 |
| 2007/0050883 | A1 * | 3/2007 | Matich | A41D 19/0089 2/69 |
| 2007/0119458 | A1 * | 5/2007 | Ging | A61M 16/0816 128/206.26 |
| 2008/0110469 | A1 * | 5/2008 | Weinberg | A41D 13/1176 128/863 |
| 2008/0229929 | A1 * | 9/2008 | Marcoon | B01D 46/10 96/296 |
| 2008/0257354 | A1 * | 10/2008 | Davidson | A61M 16/06 128/206.24 |
| 2008/0302365 | A1 * | 12/2008 | Cohen | A61M 16/0616 128/206.12 |
| 2009/0035390 | A1 * | 2/2009 | Modak | A61K 33/30 424/641 |
| 2009/0139525 | A1 * | 6/2009 | Schirm | A61M 16/0605 128/205.25 |
| 2009/0211581 | A1 * | 8/2009 | Bansal | B32B 5/026 128/206.19 |
| 2009/0293880 | A1 * | 12/2009 | Rutan | A61B 5/097 128/206.21 |
| 2010/0031958 | A1 * | 2/2010 | Stewart | A62B 18/08 128/203.29 |
| 2010/0282265 | A1 * | 11/2010 | Melidis | A61M 16/0611 128/206.26 |
| 2010/0326445 | A1 * | 12/2010 | Veliss | A61M 16/06 128/206.24 |
| 2011/0005524 | A1 * | 1/2011 | Veliss | A61M 16/0655 128/206.24 |
| 2011/0061656 | A1 * | 3/2011 | Matich | A62B 23/025 128/206.25 |
| 2012/0180794 | A1 * | 7/2012 | Smart | A61M 16/085 128/205.25 |
| 2012/0180795 | A1 * | 7/2012 | Knight | A61M 16/0683 128/206.24 |

(56) References Cited

U.S. PATENT DOCUMENTS

| | | | | |
|---|---|---|---|---|
| 2012/0204881 | A1* | 8/2012 | Davidson | A61M 16/0683 |
| | | | | 128/206.25 |
| 2013/0139829 | A1* | 6/2013 | Rutan | A61B 5/097 |
| | | | | 128/863 |
| 2014/0150799 | A1* | 6/2014 | Daly | A61M 16/0688 |
| | | | | 128/206.25 |
| 2014/0190492 | A1* | 7/2014 | Noh | A41D 13/1176 |
| | | | | 128/863 |
| 2014/0345621 | A1* | 11/2014 | Zack | A61M 16/0605 |
| | | | | 128/206.24 |
| 2014/0354941 | A1* | 12/2014 | Chang | G02C 3/003 |
| | | | | 351/137 |
| 2015/0352309 | A1* | 12/2015 | Daly | A61M 16/0688 |
| | | | | 128/206.25 |
| 2015/0374943 | A1* | 12/2015 | Alexani | A61M 16/0688 |
| | | | | 128/206.24 |
| 2016/0339196 | A1* | 11/2016 | Bowsher | A61M 16/0622 |
| 2017/0049983 | A1* | 2/2017 | Ellis | B32B 5/26 |
| 2019/0001093 | A1* | 1/2019 | Rutan | A61M 16/0616 |

\* cited by examiner

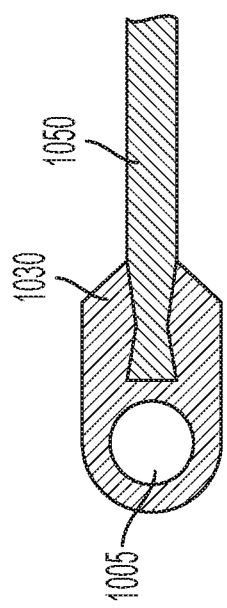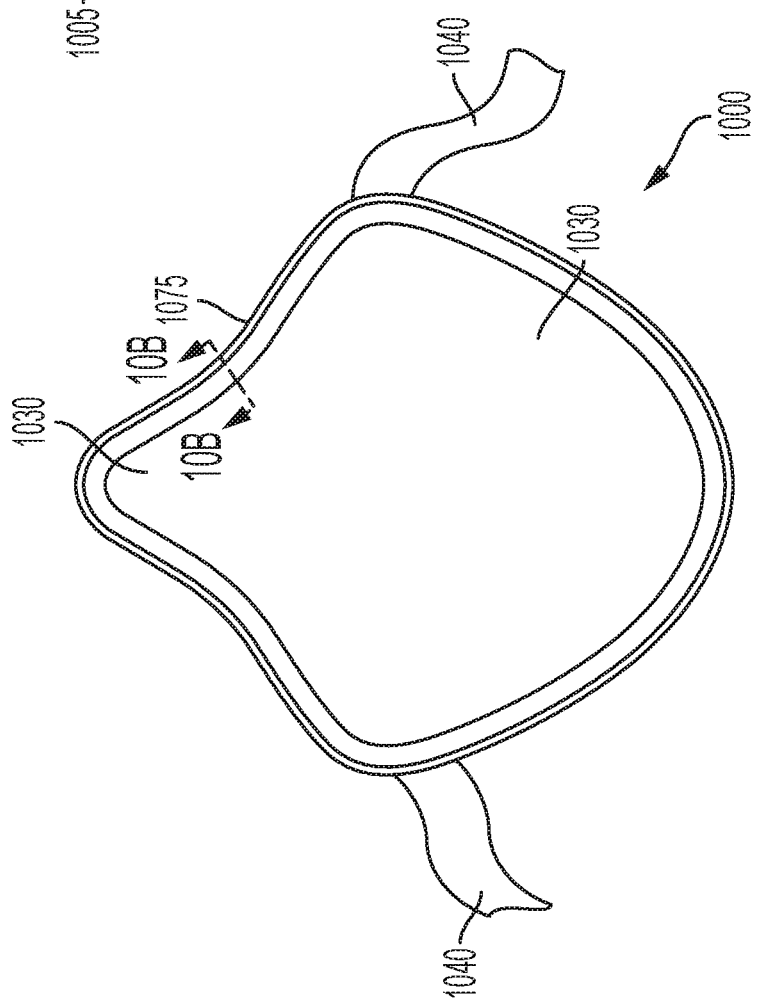

SOFT SILICONE EDGED CUSHION FOR FACE MASKS

This application is a continuation of U.S. patent application Ser. No. 16/880,496 filed May 21, 2020 and claims the benefit of priority to U.S. Provisional Patent Application Ser. No. 63/027,208 filed May 19, 2020, entitled "The Soft Silicon Edged Cushion for Face Masks," by the same inventor.

FIELD OF THE INVENTION

The present invention generally relates to the technical field of apparatus and a method for protecting the face of a healthcare worker, a patient requiring use of a ventilator or an oxygen mask, a surgeon desirous of a safe and comfortable surgical mask, or emergency technical personnel requiring protection from damage during prolonged use of a face mask and, more particularly, to apparatus comprising a semicircular, flexible U-shaped or mostly circular cross-section of tubing or a shell comprising a soft silicone edged cushion that may hold a soft medical gel or jelly material or permit the soft gel material to coat both the tubing or shell and a cloth surface or protect a lateral edge of the face mask so as to protect a user from facial damage or discomfort.

BACKGROUND OF THE INVENTION

CNN interviewed Dr. Sanjay Gupta, medical advisor to CNN, on Jul. 24, 2020. During the CNN interview, Gupta is quoted as saying: "We're basically told to reuse the same mask as long as we can." In answer to a question of an interviewer, Dr. Gupta stated: "So the mask, just not that this matters as much, but you're wearing this mask doing a five, six hour operation. If you're wearing it properly with a fit test, it digs into your face. It hurts after a while. But you do everything to protect it; it's like gold. So I'll wear another mask on top of it, to prevent that N95 mask from being contaminated."

Across the United States and internationally, local, state and federal governments are recommending the use of social distancing and related face masks to safeguard from a pandemic related to corona virus or Covid-19. Despite weeks of conflicting, and often confusing information on the effectiveness of face masks of all types for public use, the Center for Disease Control and Prevention (CDC) recommends that everyone wear face masks. A face mask may be defined for the purposes of this patent application as any variation of a mask that is intended to cover the mouth and nose to protect against inhalation or other exposure to virus pathogens. The face mask may be a surgical mask, a mask of hard rubber or plastic material (for example, an oxygen mask or a ventilator mask), a cloth mask produced from several layers of a cloth material. One or more layers may be capable of bonding to and holding incoming pathogens and the like preventing them from being inhaled. According to the CDC, "cloth face coverings should: fit snugly but comfortably against the side of the face; be secured with ties or ear loops; include multiple layers of fabric; and allow for breathing without restriction." In particular, cloth masks are recommended for general use and surgical masks and N95 respirators manufactured, for example, by 3M since 1972 are recommended for use by healthcare workers. The N in N95 denotes a rating that does not protect against oil-based aerosols but is highly recommended for use by healthcare workers. The 95 represents the percent of 0.3 micron particles removed from air that is inhaled through the face mask.

Hospitals have also used oxygen masks or ventilators to deliver pathogen-free oxygen through the nose in acute or intensive care units. For the present purposes, an oxygen mask or a ventilator may cause problems with comfort of the mask/ventilator, and such an oxygen mask or ventilator device is encompassed by the present patent application.

People who go to public places such as grocery stores may wear disposable cloth masks while healthcare workers may, for example, use N95 respirators and surgical masks. Whether one is a member of the public or a healthcare worker, a mask should completely cover the mouth and nose and preclude the admission of air through gaps in the cloth caused by inappropriate use of a cloth mask or the rigidity of a mask made from solid material such as a ventilator or oxygen mask. At the same time, masks (as opposed to handkerchiefs, bandanas and make-shift face masks) should be avoided because air and liquid droplets of pathogens may not be absorbed by the single layer of cloth and may enter via the chin or other unprotected areas of the face.

The general public who use their masks when in the bright sunshine and wear sun-glasses or are required to wear eyeglasses to drive or ride in a vehicle will exhale warm, moist air through a cloth mask and quickly learn that their eyeglasses with fog up and cause them to lose sight. Some face masks are designed to provide for wire (small gauge aluminum or copper wire, for example, insertion at the edges of a mask; some have shaped sponges for shields, for example, around the nose. These may require manipulation to avoid discomfort or escape of air toward the eyes (and so protect against foggy eyeglasses).

Many people fail to use proper masks and choose to use handkerchiefs or scarves tied behind their faces which may permit air into openings, for example, when simply tied behind one's neck and receive air, for example, or pathogens from an opening under one's chin. On the other hand, the elastic used in forcing a pre-structured oxygen or ventilator mask of hardened rubber or plastic to cover the many different shapes of faces (everyone's face is differently shaped from one another) can cause facial damage and still be ineffective in covering gaps in an effort to cover one's mouth and nose. If one's mask does not fit properly, one will be constantly adjusting the mask and may touch their face exposing them to a viral infection having touched These masks may have strong elastic ties to one's ears or around the head. When one wears such a mask for a long period of time, the elastic strength may cause irritation, rashes, markings and general discomfort around its edges.

Wearing face masks are now an important part of our everyday lives. However, wearing face masks for long periods of time can cause skin issues and irritation. Dermatologists studying the issue of lengthy use, for example, the same mask all day, will irritate facial skin, clog pores, cause acne, rosacea and dermatitis. Also, healthcare workers are under a lot of stress as they go about their daily duties of, for example, intubation, inserting oxygen tubes into a nose of a Covid-19 patient or the stress of an operating room or an intensive care unit.

An N95 mask tightened onto the face puts all the pressure of, for example, a pair strong elastic or rubber straps for tying the mask to the ears or the back of the head onto the soft facial tissue that is in contact with the mask's edge, especially a mask made of hard rubber or plastic. Researchers have calculated that the resulting pressure from medical masks can be greater than an equivalent of three pounds per square inch on the face's soft tissue. A medical worker wearing such a mask all day will likely suffer from the edges of the mask and may want to be careful about choosing the shape of a mask for a twelve-hour shift.

Overly dry skin can lead to skin inflammation due to cracks and fissures while facial skin may sweat and masks may be used in humid conditions and so one's skin may be susceptible to irritation. A moisturizing cream may help some with dry skin but a moisturizing cream is not designed to prevent air from leaking from edges of a face mask.

U.S. Pat. No. 9,963,611 (the '611 patent) to Stewart et al. describes a composition (for example, of multiple layers of different types of cloth) and at least two different masks. One type of mask is seen in FIG. 1, FIG. 2 and FIG. 13 for use as a face mask to shield against viral pathogens. The mask may comprise lateral edge and looped with a loop extension from the lateral edges to wearing on one's ears. A top edge protects the nasal area while a larger body protects, the mouth and nose.

A second embodiment of a type of facial mask is shown in FIGS. 3 and 4 of the '611 patent (with a resilient member that may be a foam or deformable strip adjusted by the wearer and flap for contour about the nose), comprising as seen in FIGS. 5, 6, 7 and especially FIG. 8 how the mask may comprise a flap and sides that may be stitched together to protect the faced with having to manipulate the mask to exclude pathogens from reaching the nose and mouth. As seen in FIGS. 9 through 12 of U.S. Pat. No. 9,963,611 of Stewart et al., the mask may comprise as many as four or more layers of different absorbent materials, at least one layer for capturing and bonding to pathogens. FIGS. 1 and 2 show typical disposable face masks with loops 14 to tie the face mask to one's ears. Lateral edges 30 have a perpendicular connection to a top edge and bottom body 12. On the other hand, FIGS. 3-8 show a mask which has lateral edges which are more adaptable to being protected and include a flap 104 and a resilient member 142 for fitting above the nose bridge.

Prior art FIG. 1 of the present patent application shows a woman wearing a typical oxygen face mask comprising a plastic nose and mouth covering 100. The lateral edge of the plastic covering 100 is hard and may damage the face. The figure appears to show the use of an elastic band which surrounds the rear of her head above her ears and may help to lift and hold the tube attached to the mask which serves as an oxygen supple. There is a plastic lateral edge 125 which being held to the face by elastic can cause discomfort. There also appears to be a hardened plastic nose bridge contoured to prevent oxygen from escaping to reach her eyes.

Prior art FIG. 2 shows a patient lying in a bed wearing a ventilator mask 200 which appears to comprise plastic or a hardened medical silicone. Like the oxygen mask 100, the ventilator mask 200 appears to have a hardened plastic or silicone lateral edge 225 held by elastic bands to the face of the male patient. Also, it appears from the drawing that the patient is in discomfort and may have puffy cheeks caused by long term use of the ventilator mask 200. The oxygen appears to be delivered by a tube directly to the nasal area of the patient.

Prior art FIG. 3 shows the exterior of a typical 3M N95 rated mask 300 typically worn by healthcare workers. The lateral edges 320 are made of cloth material and appear to be held to the face by pairs of elastic straps. Healthcare workers may wear their masks for twelve hour shifts. After twelve hours, there may be considerable discomfort from wearing the mask. Also, the cloth lateral edges 320 may capture air on inhalation and release air on exhalation. A healthcare worker may have a need to adjust the mask frequently due to the use of the cloth to snuggly fit over the nose and mouth.

Prior art FIG. 4 shows the interior of the 3M N95 rated mask 400. The interior includes a breathing grid 415 and also includes a foam rubber nose bridge 410. The foam rubber nose bridge 410 may cause some discomfort from a wearer's moving their head especially over a twelve hour shift period.

From measuring the circumference of lateral edges of prior art face masks of the prior art types described above, the circumferences of prior art masks all appear td be approximately the same. As will be discussed below, the similar circumferences may be utilized to advantage in the present invention.

There remains in the art a need to solve the problems caused by the use of sharp-edged plastics, cloths, silicone and rubber materials for a face mask with elastic rubber or string ties to the ears or surrounding the head that can cause considerable discomfort, even some forms of disease and sores to develop that cannot be treated with moisturizing cream alone or the use of deformable strips, resilient members and wires embedded in edges of cloth face masks, surgical masks or oxygen masks or ventilators.

SUMMARY OF THE EMBODIMENTS

The present invention solves the comfort and protection problems of prior art face mask designs. An embodiment of the face mask protection is designed to comprise a U-shaped member (or one that is semi-circular or almost circular) and a soft gel type material such as a medical silicone (Shore A on the hardness scale) that may be fixed to the lateral edges of a face mask that may or may not contain deformable wires that a user may shape to the contours of their face or nose. From investigation, it has been determined as indicated above that most face masks have the same or similar circumference (for example, the length of the cloth material comprising the lateral edges of a 3M N95 face mask shown in prior art FIGS. 3 and 4). A medical grade silicone is selected according to a Shore hardness scale to be deformable but tight enough so as to fit permanently around the lateral edges of most face masks such as a Shore A hardness scale between 10 and 40, preferably approximately 25. An outer shell may contain the medical soft gel material and when coated on the inside with a petroleum jelly or Shore A 0 gel or jelly will wet or protect any exterior cloth lateral edges. Of importance, also, is the coating on the interior of the U-shaped or circular member with a soft medical silicone gel or petroleum jelly so that the soft gel serves at least two purposes. A first purpose is to wet or render leak-proof a lateral edge, for example, comprising cloth to prevent leakage of airborne pathogens to the facial area. Ideally, a face mask should not be moved once applied to the face. The movement may alleviate discomfort but cause leakage of airborne pathogens to the face. A second purpose is comfort. When a U-channel, circular or clasping soft cushion covering covers the lateral edges, any discomfort brought on by use of elastic straps or string ties with movement of the face and head may be alleviated.

Special provisions may be used in the nasal area to provide a protection of nasal exhalations from rising upward toward the eyes of the wearer, especially to prevent fogging of eyeglasses. While foam rubber is known used in N95 masks and a nose plate is known from the oxygen and ventilator masks of FIGS. 1 and 2, these can be uncomfortable and replaced by deformable nose bridges coated with petroleum jelly or medical 0 hardness silicone gel. The coating also should also prevent the wearer from suffering any long-term adverse reactions to the coating and be medically safe.

These and other features of the present invention will be made clear from the Brief Description of the Drawings which follows along with the Detailed Description which follows the brief description.

BRIEF DESCRIPTION OF THE DRAWINGS

A convention is used with the drawings of the present invention such that the first number of a reference numeral such as 100 represents the figure number of the item where a particular component 10X first appears where X is intended to comprise a similar component in a later discussed figure.

FIG. 10A shows a typical face mask 1000 in front view which may be any of an oxygen mask, a ventilator mask, a disposable face mask or a surgical mask 1000 having been manually fitted around lateral edges of the mask 1050. A soft U-shaped medical silicone for clasping the lateral edges of the mask 1030 is continuous and is manually fitted to the lateral edges of the mask 1050.

FIG. 10B shows FIG. 10A in cross-section at a lateral edge of the mask 1050 such that the soft U-shaped medical silicone section 1030 clasps the mask at lateral edge 1050.

Now a detailed description of FIGS. 1-10B will be provided having briefly described the present invention,

DETAILED DESCRIPTION

The present invention is directed to a face mask, face and nose protector that provides greater comfort to the wearer and prevents leakage of exhaled air form the lateral edges of the face mask which will be described with reference to FIGS. 1-10B.

Figure 1:
FIG. 1 shows an example of a prior art oxygen face mask 100 having a lateral edge 125 that appears to comprise plastic that can be elastically tied to the face. The pressure caused by the elastic or material ties around the head may cause discomfort in the regions of the face protected by lateral edges 125. The oxygen face mask 100, being solid, may not fit the wearer such that oxygen leakage is avoided.

FIG. 1 shows an example of a prior art oxygen face mask 100 having a lateral edge 125 that appears to comprise plastic. The face mask 100 with its surrounding lateral edges 125 can be elastically tied to the face. The pressure caused by the elastic or material ties around the head may cause discomfort. The oxygen face mask 100 being solid, may not fit the wearer so that the mask is comfortable to wear and such that oxygen leakage from the lateral edges 125 may be avoided. Notice also that there appears to be a nose bridge for preventing a loss of oxygen in the direction of the eyes. As will be discussed herein with reference to FIGS. 6-10B, a soft cushion shell of the present invention provides a soft gel internal to the soft cushion shell that is intended to relieve discomfort and prevent air from escaping from lateral edges of, for example, a face mask comprising an oxygen mask.

If this patient were to wear this mask 100, as is, all day long and night, with apparently plastic edges, it is highly likely that the patient will have discomfort. The wearer may develop skin conditions form wearing the mask for long intervals, perhaps abrasions or even contusions. It is a feature of the present invention to provide a soft cushion shell that fits over the edge and protects the wearers face, adapted to be used with a coating for contacting the mask and a coating for contacting the face underneath the shell for clasping the mask to protect form leakage of oxygen to the air and promote comfort.

Figure 2:
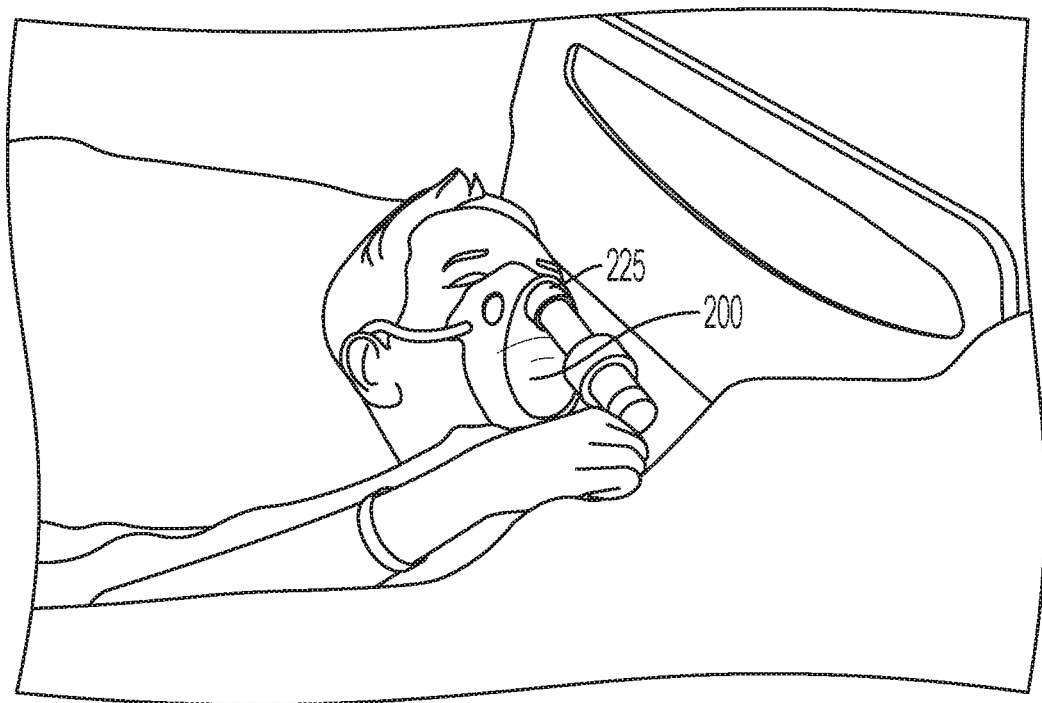
FIG. 2 shows a prior art ventilator face mask 200 which may also comprise a solid plastic lateral edge 225 that may rub against the skin and irritate the facial regions where the lateral edges 225 are pulled tight or even cause some forms of disease. The purpose of the ventilator is to deliver and potentially force air into the lungs for a person having difficulty breathing. Adjustable elastic straps may hold the mask to one's face, but the patient may be forced to rest in one position in order to safely and comfortably wear this ventilator mask.

FIG. 2 shows a prior art ventilator face mask 200 which may also comprise a solid plastic edge 225 that may rub against the skin and irritate the skin. The purpose of the ventilator is to deliver and potentially force air into the lungs for a person having difficulty breathing. Adjustable elastic straps may hold the mask to one's face. The pressure caused by the elastic or cloth material ties around the head may cause discomfort where the lateral edges contact the face. The ventilator face mask 200 being made of a solid material such as plastic, may not fit the wearer such that oxygen leakage can be avoided. A soft cushion shell may be provided as will be discussed with reference to FIGS. 6-10B comprising a medical silicone shell component that contains a soft gel or jelly that is intended to relieve discomfort and prevent air from escaping from lateral edges of, for example, a face mask comprising an oxygen mask. Also, the shell may be coated with a soft gel or petroleum jelly that alleviate a patient's facial discomfort.

In other words, the ventilator mask shown, appears to be very similar to the oxygen mask of FIG. 1. The patient appears to exhibit some swelling in his face around the mask 200, perhaps caused by the lateral edges 225 which can be avoided by using a soft cushion tubing like structure with soft gel that can protect the face and prevent oxygen leakage.

Figure 3:
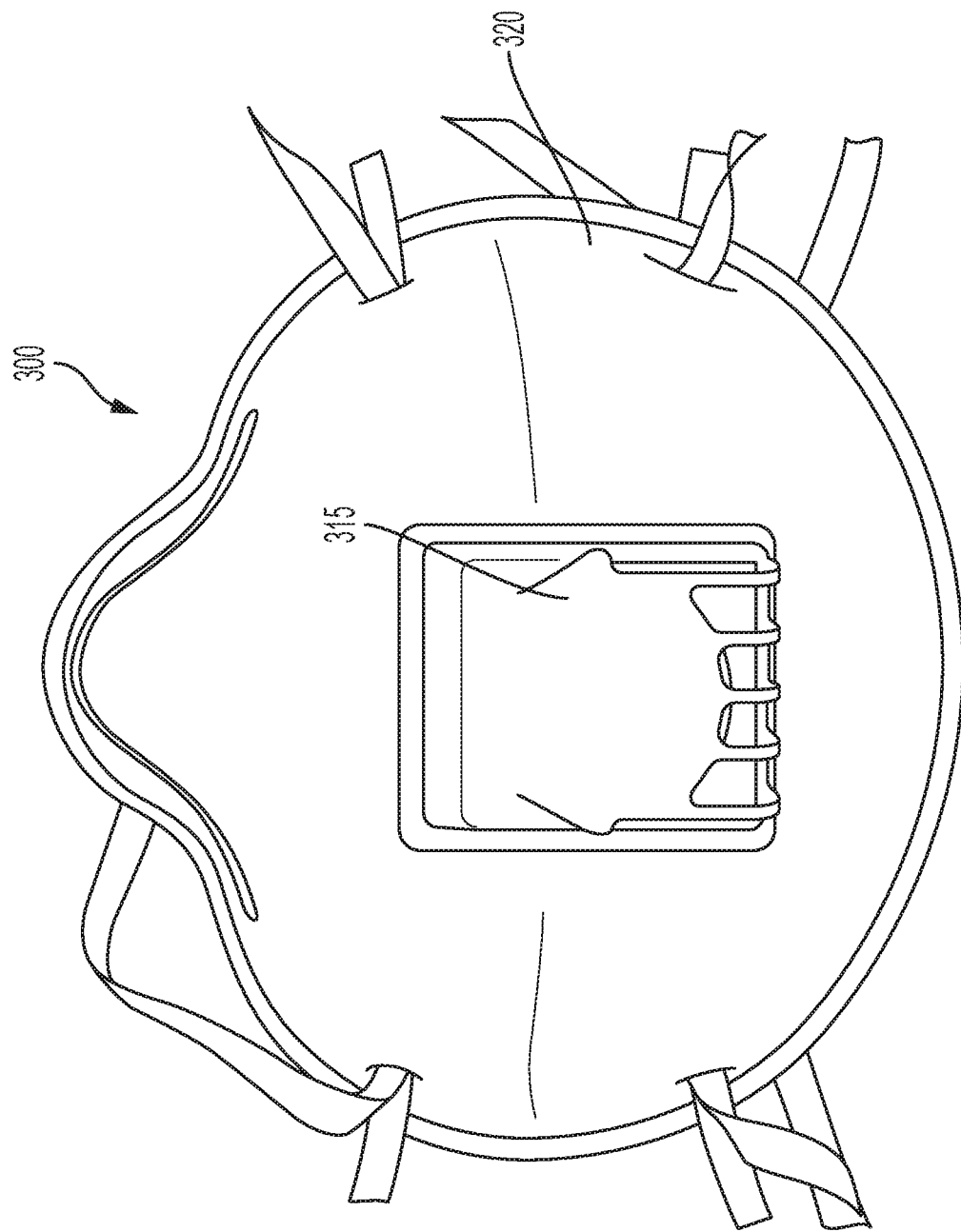
FIG. 3 shows a front view 300 of a 3M N95 rated face mask. Of importance is the circumference of the face mask comprising a flexible border soft material (lateral edge 320) which may allow leakage of air to the nose and fails to form a tight seal against leakage of viral pathogens to the exterior. less). A nose grid 315 comprises a filter for the mask and the mask is especially recommended for healthcare workers.

FIG. 3 shows a front view 300 of a prior art 3M N95 rated face mask. Of importance is the circumference of the face mask comprising a flexible border soft cloth material which may allow leakage of air intended to be inhaled by the mouth or nose. The lateral edges 320 form a circumference that fails to form a tight seal against leakage of viral pathogens to the exterior. A filter grid 315 and cloth material is shown which is intended for air or oxygen inhalation and exhalation. The material forming the mask may be multi-layers so that 95% of small viral pathogens on the order of three microns cannot enter the mask and reach the patient.

The N95 face mask is most popular for use by healthcare workers in hospitals and wards when they are working closely with diseased patients. The cloth material lateral edges may be adapted to receive a soft cushion shell according to the present invention that is elastic and of sufficient circumference to reach around the entire mask. As with FIGS. 1, 2, and 3, please refer to FIGS. 6-10B for an explanation of the present invention.

Figure 4:
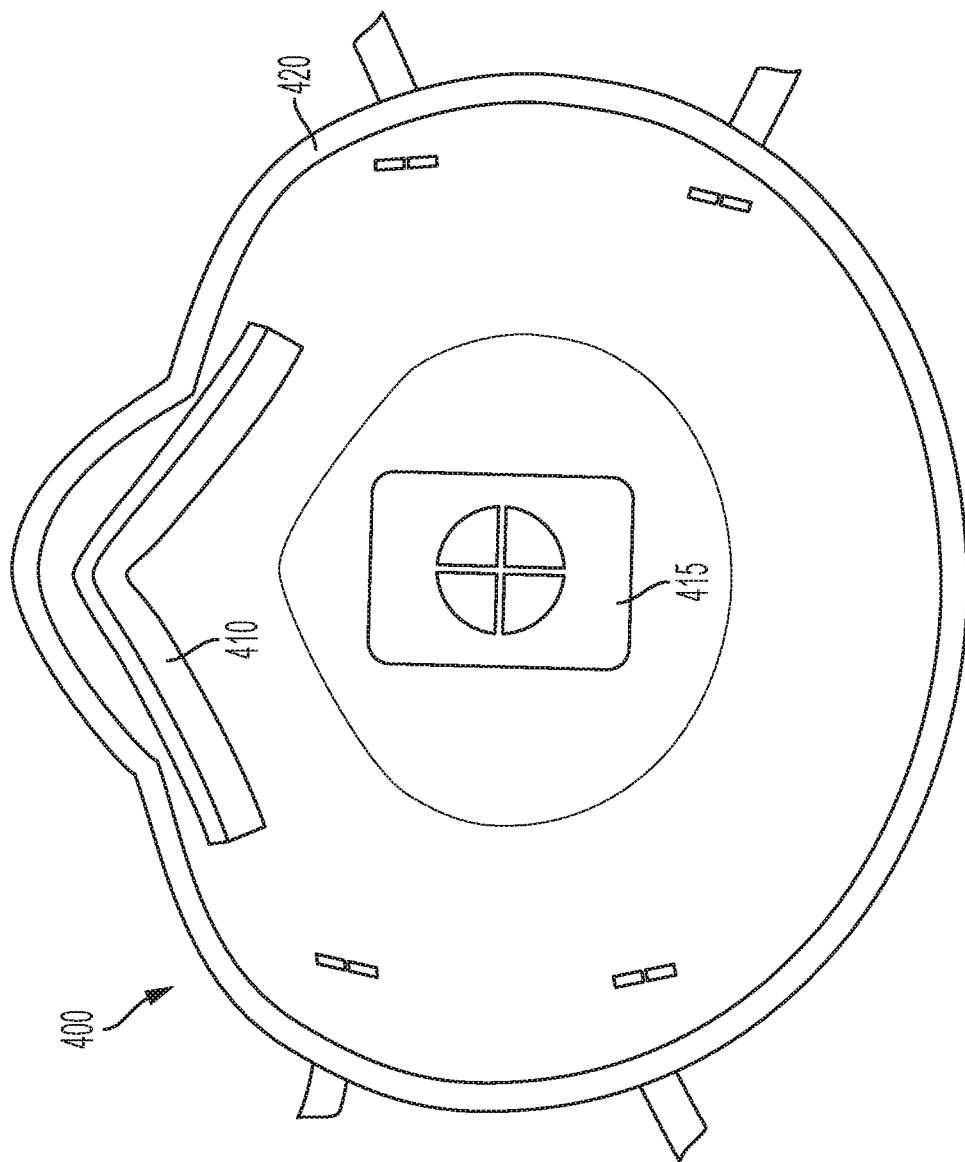
FIG. 4 shows a rear view 400 of the 3M N95 rated face mask example face mask 300 of FIG. 3. Notice that there is a grid 415 (the opposite side of grid/filter 315 of FIG. 3) for receiving air from the exterior, filtering the inhaled air and emitting breathed air to the exterior. In addition, a foam rubber nose bridge 410 may be formed to prevent breathed air from rising above the nose to the eyes of the wearer. The foam nose bridge 410 may or may not effectively prevent a wearer of the face mask who wears eye glasses from having their glasses fog.

FIG. 4 shows a rear view 400 of the 3M N95 rated face mask example face mask 300 of FIG. 3. Notice that there is a grid 415 (the reverse side of grid/filter 315) for receiving air from the exterior, filtering the inhaled air and emitting breathed air to the exterior. In addition, a foam nose bridge 410 may be formed to prevent breathed air from rising above the nose to the eyes of the wearer. The foam rubber nose bridge 410 may or may not effectively prevent a wearer of the face mask who wears eyeglasses from having their glasses fog.

According to the present invention as described by FIGS. 6-10B, the lateral edges 420 are sealed by a clasping elastic shell that fits the entire circumference of the lateral edge. Also, the foam rubber bridge, if detrimental to the patient, may be fitted with a nose bridge constructed similarly to the protective and wetting shell soft cushion, for example, of medical silicone gel.

Figure 5A:
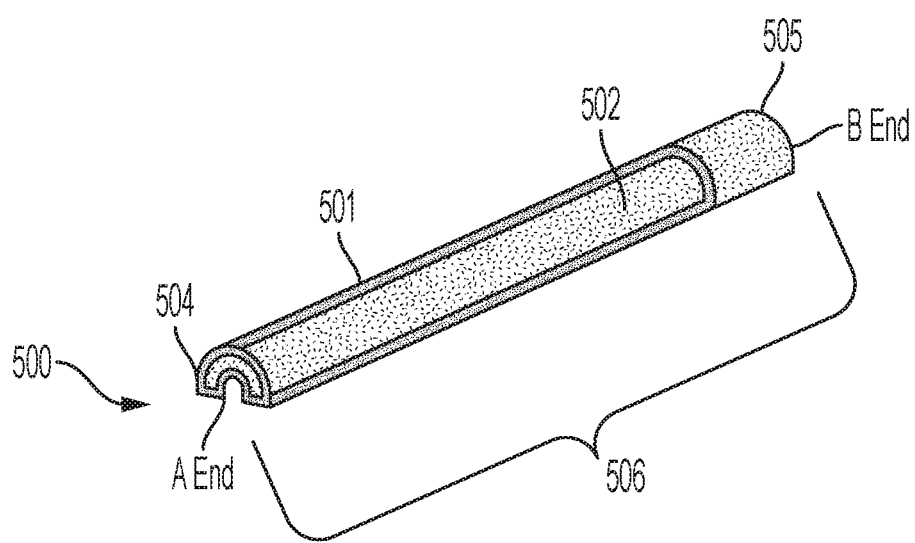
FIG. 5A shows a cross-section 500 of a U-shaped or semi-circular shaped exterior shell of apparatus for surrounding the lateral edges of a face mask, for example, face masks 100, 200, 300 and 400 of prior art FIGS. 1, 2, 3 and 4. In one embodiment, the exterior shell 501 has a semi-circular or U-shaped cross-section which will be discussed with respect to prototype FIG. 10. Other useful shapes are a clam or clasping shape (like a clam shell). Inside the exterior shell 501, the shell preferably contains a soft gel, jelly or petroleum jelly 502 which is malleable and in combination with the shell 501 may be used the clasp the lateral edges of, for example, the entire circumference of an N95 face mask. Reference numerals 504, 505 are A and B ends intended to show insertion of soft silicone medical grade gel into shell 501. Reference numeral 506 may represent that the cross-section 504 or 506 may be tapered, molded, plugged or clasped together and to a cloth material such as the lateral edges of an N95 cloth mask. As will be discussed with reference to FIG. 10, a continuous circle of cross-section 504 may be manipulated by the user to 1) coat the interior with petroleum jelly or soft silicone gel so as to wet the N95 cloth lateral edges.

FIG. 5A shows a cross-section 500 of a U-shaped or semi-circular shaped exterior shell of apparatus for surrounding the lateral edges of a face mask, for example, N95 face masks 300 and 400 of FIGS. 3 and 4. In one embodiment, the exterior shell has a semi-circular or U-shaped cross-section which will be discussed with respect to prototype FIGS. 10A and 10B. Inside the exterior shell coating 501, for example, of Shore A extra soft hardness 10-40 (see FIG. 5B for a Shore A hardness scale), the shell preferably contains a soft gel 502 which is malleable and in combination with the shell 501 is used the clasp the lateral edges of, for example, the entire circumference of an N95 face mask, oxygen mask or ventilator mask (or surgical mask, not shown). See FIGS. 10A and 10B. Reference numeral 504, an A end, for fitting to a B end 505 is intended to indicate ends of a shell 501 that are formed to meet one another during injection molding in one embodiment that is made just for one common mask. In another mode of manufacture, by using a plug, by tapering one end to fit into the other or other means, a measured length of U-channel may be fitted to fit the lateral edge of any face mask. For example, an A end may fit into a pocket formed in the B end to receive the A end such that a typical circumference of a lateral edge of a face mask may be covered by the shell clasping the lateral edges having been hand-fitted around the mask to match its circumference. See FIGS. 10A and 10B.

One of many known injection molding processes may be used for forming a complete unit for fitting a given mask or for making a self-installable sized mask that may have A and B ends for plugging into one another. During injection molding processes, the cushion around a face mask may be manufactured as a complete circumference designed to fit a particular mask such as an N95 mask having a predetermined circumference of lateral edging. Per FIG. 5, when injection molding is used to process the soft gel part 502, 505 of the cushion, the gel part 505 may be inserted may be inserted into the cushion. Alternatively, the A end 504 of U-channel, semi-circular cushion having length 506 may be tapered to fit in the B-end 505. Outside air cannot enter the U-shaped channel. Also, air or water may be inserted into the U-channel 501 in place of soft gel or other similar material. Component 502 may be an extra soft gel or jelly material of a Shore A hardness of extra soft or in the range of 0 to 10 if comprised of medical silicone quality gel. As will be further described herein, the internal material 502 may be air or water. Reference numeral 505 is intended to show the insertion of soft gel 502 within the shell 501. Length 506 is intended to be the typical circumference of a face mask. From measuring the circumference of various types of face masks, it has been determined that most face masks have the same overall circumference. In other words, one size soft cushion will fit most face masks.

Figure 5B:
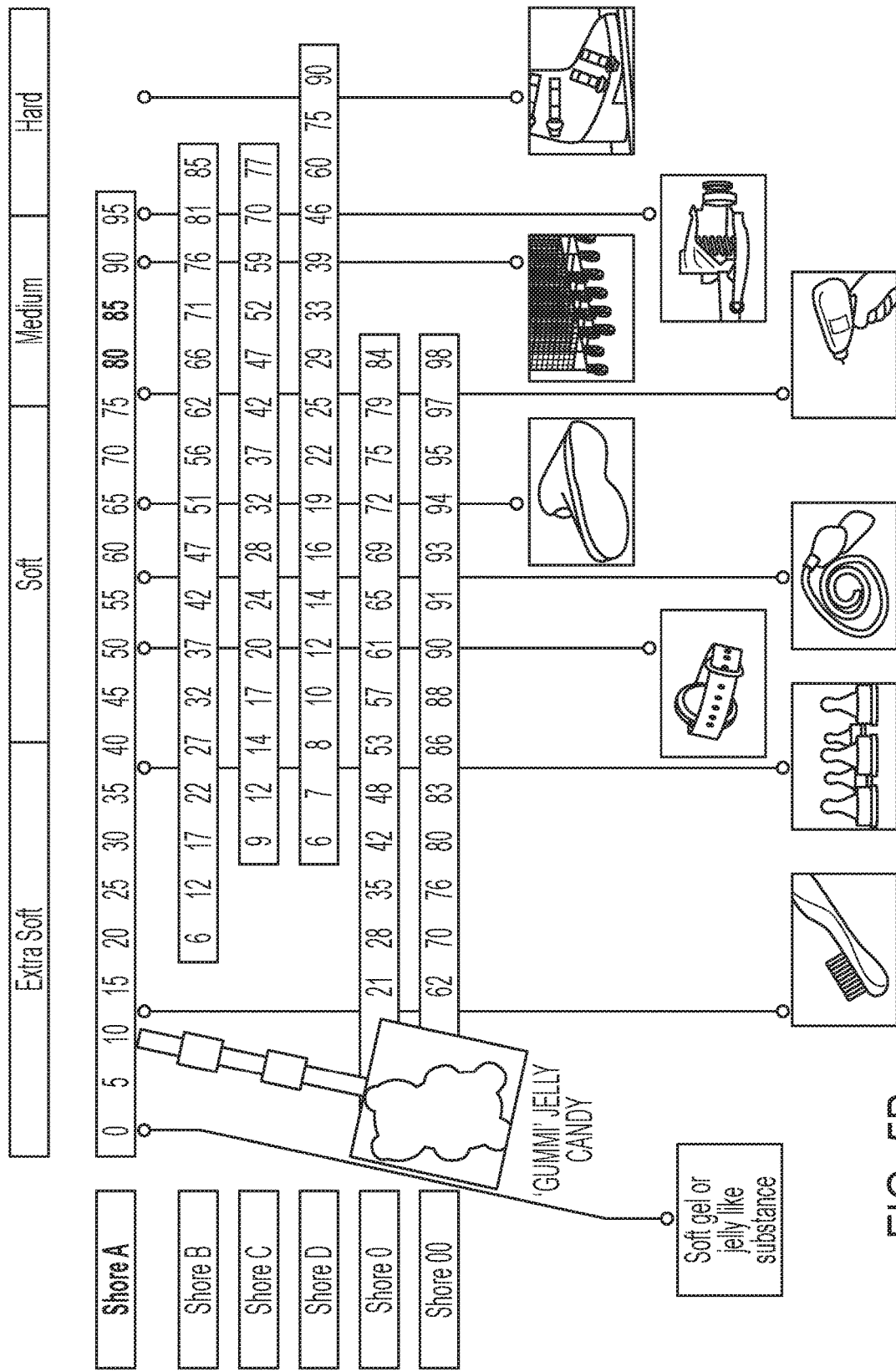
FIG. 5B is an expanded view of a Shore A-00 hardness scale and examples of uses of silicone for a substance such as a soft gel or jelly-like substance that may be used as a coating or a filler from "extra soft" to hard. Silicone in the lower hardness numbers such as 10-40 may have elastic qualities allowing the silicone to be stretched and manually coated inside and out to protect the face and to grasp the lateral edges of the face mask.

FIG. 5B shows a Shore hardness scale used by manufacturers of medical silicone gel to qualify the hardness of silicone material. The Shore hardness is intended to be between 00A and 40A of a durometer scale for both soft gel or a jelly like substance interior and a hardness between a range of 10-40 on the extra soft Shore A Hardness scale for the exterior shell like clasping component 501. Preferably, the shell 501 will have a greater Shore hardness that is harder than the soft gel interior or coating 502 so that is elastic and formable as it covers the lateral edges of a face mask of any type.

Figure 6:
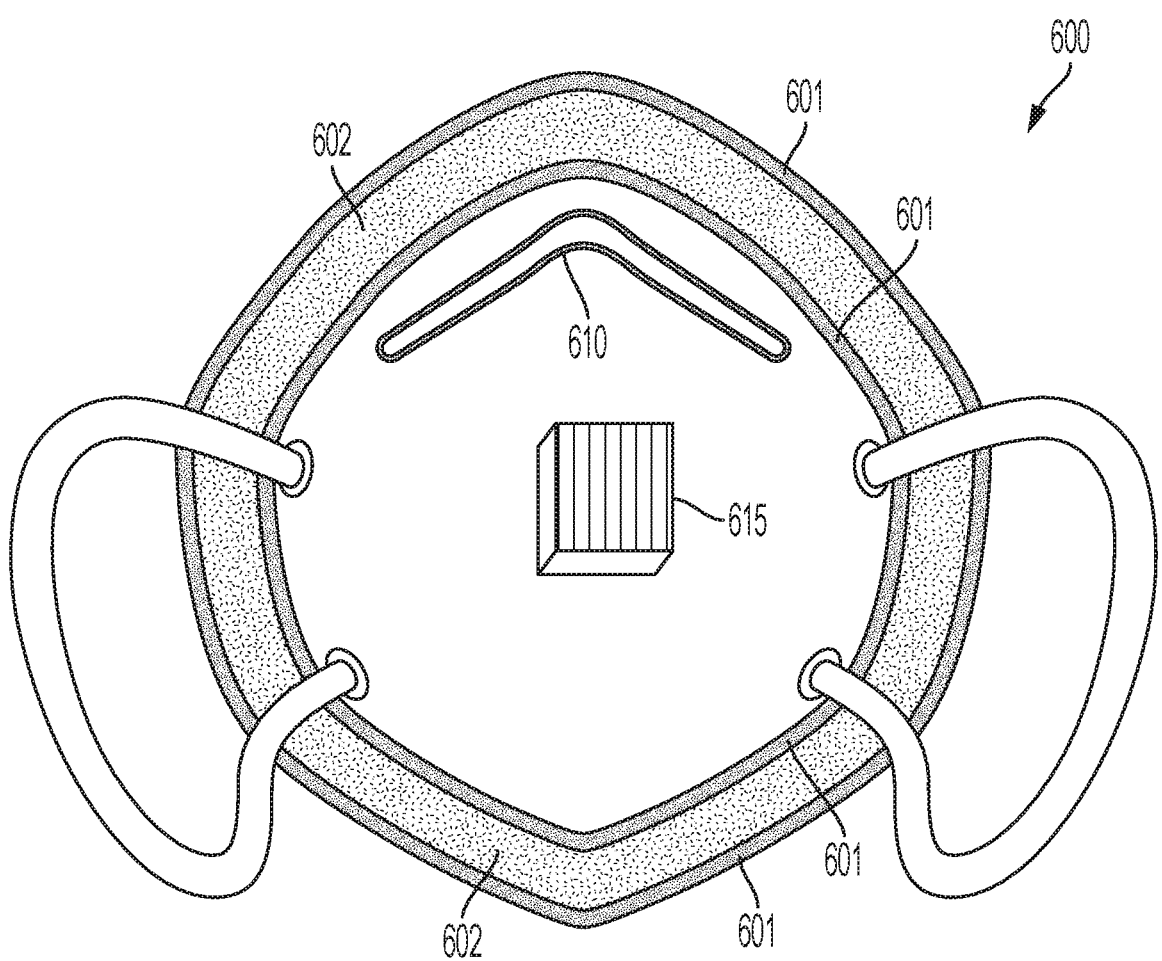
FIG. 6 shows a detailed cross-section example of a typical interior of an N95 face mask 600 fitted with a U-shaped or semi-circular shaped or circular shaped shell 601 (shown in cross-section) which clasps cloth lateral edge material of the N95 mask (not shown). Interior soft gel 602 serves to moistens the fabric or cloth of lateral edges of the N95 mask and exterior soft gel 602 wetting the cloth material lateral edges prevents air leakage and while exterior soft gel 602 coating the shell 601 promotes a comfortable fit to the face. Nose bridge 610 is shown as in FIG. 4 comprising foam rubber but may be coated with petroleum jelly or soft gel 602.

FIG. 6 shows a detailed cross-section example of a typical interior of an N95 face mask fitted with a U-shaped or semi-circular shaped or circular shaped shell 601 which is elastic but may clasp cloth lateral edge material (not shown in this figure). Interior soft gel 602 may be used on the exterior to moisten fabric of lateral edges, prevent air leakage and promote a comfortable fit to the face. Interior gel 602 may alternatively comprise water or air or other medically safe liquid or gas. Nose bridge 610 is shown as in FIG. 4 comprising foam rubber that may be clasped by, for example, a U-shaped cross-section 601, 602 and coated on its exterior with soft gel or petroleum jelly (or other medically safe lubricant) to seal the nose bridge and be expected to be more comfortable and tighter fitting than an N95 foam rubber nose bridge.

Figure 7:
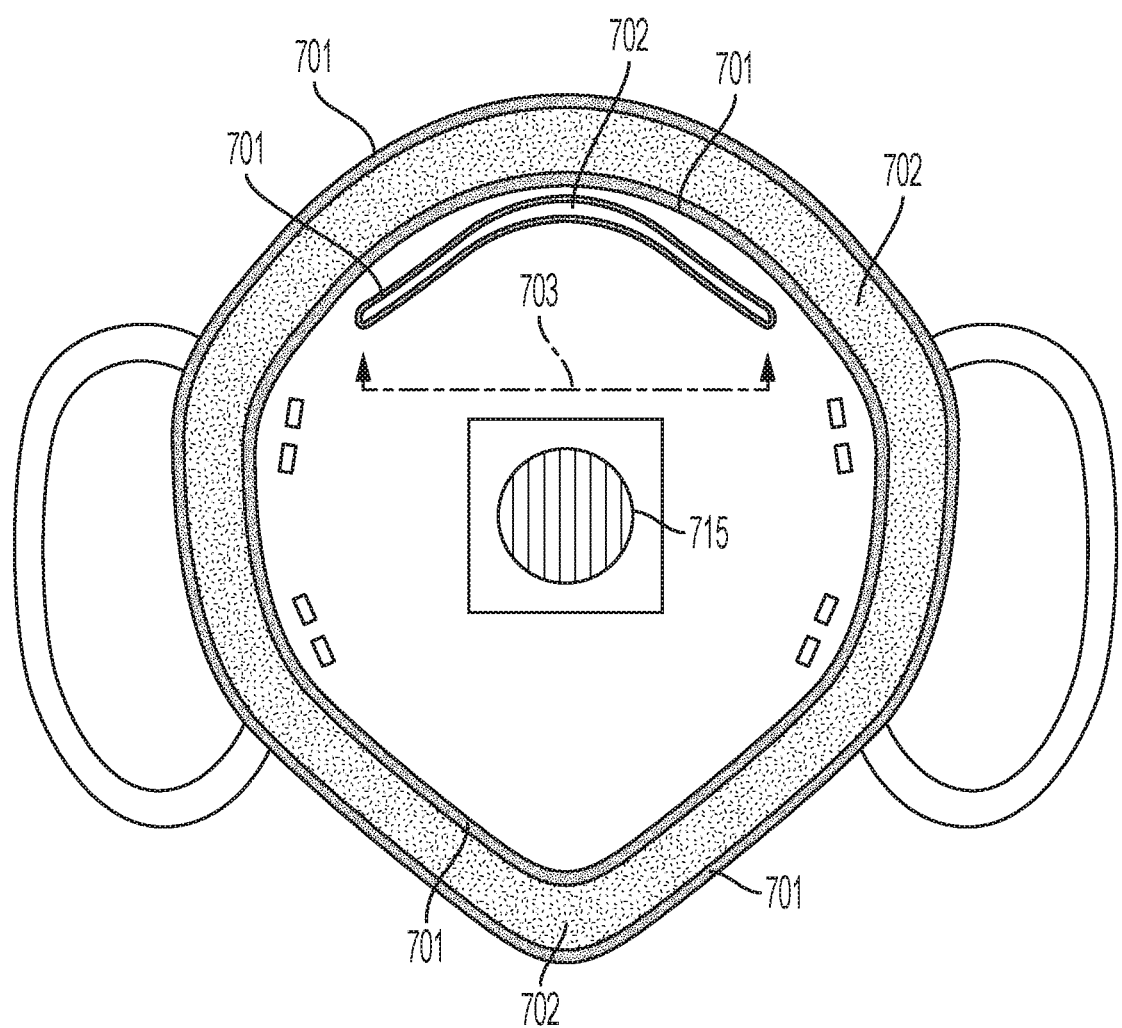
FIG. 7 provides further details of the present invention than FIG. 6 and shows a foam nose bridge of foam 410 of FIG. 4 adapted to be clasped by a nose bridge comprising shell silicone gel 701 and containing silicone gel 702. Reference numeral 703 indicates that a soft silicone edge cushion may replace prior art foam rubber as a nose bridge on the top of a wearer's nose (for example, a clasping shell 701 that clasps the existent foam rubber for comfort and to protect against air leakage to the eyes on exhalation).

FIG. 7 shows another example of an N95 face mask and provides further details of the present invention than FIG. 6, particularly regarding a nose bridge having an average length 703. FIG. 7 shows a foam nose bridge of foam 410 of FIG. 4 covered by and adapted to be clasped by a nose bridge comprising shell silicone gel 701 and containing silicone gel 702. The nose bridge 701, 702 need not be elastic as it is assumed to be of the same length as foam rubber bridge 410 of FIG. 4. The additional nose bridge 701, 702 of triangular length 703 may be coated with soft medical grade soft gel or petroleum jelly to seal the nose bridge and protect the wearer's nose from damage from rubbing foam rubber. Grid/filter 715 is shown and ear loops are shown for holding the N95 mask to the ears of a wearer.

Figure 8:
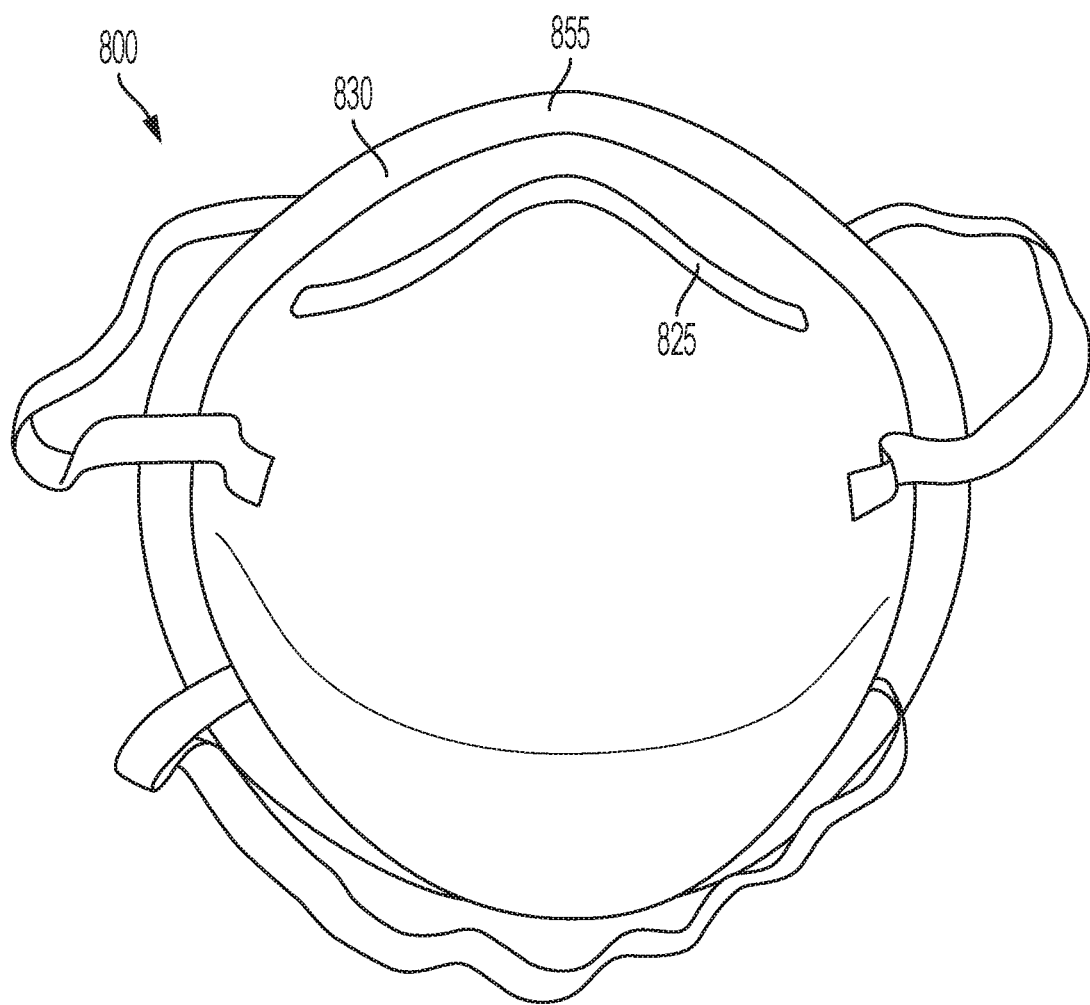
FIG. 8 provides the interior details 800 of an N95 face mask utilizing the present invention. The mouth and nose grid 415 of FIG. 4 has been removed. A U-shaped, semi-circular or mostly circular exterior shell 830 has been carefully fitted around the lateral edges of the face mask 800 such that the lateral edges have been fitted into the shell and coating 830. Note that the shell 830 is continuous and of predetermined length, is elastic and so can fit around the N95 mask lateral edges and help shape the N95 mask. Also, the foam rubber nose bridge has been replaced with a nose bridge 825 which is deformable and can conform to the bridge of the nose of a wearer by lightly pressing on the deformable nose bridge 825. The nose bridge 825 may protect the nose by a wearer applying a medical silicone gel or petroleum jelly (not shown) to the surface of the bridge 825 before placing it on the nose and adjusting its form.

FIG. 8 provides the interior details of an N95 face mask prototype 800 utilizing the present invention. The mouth and nose grid 415 has been removed. Elastic bands (which may be uncomfortable) are shown for the ears and to fit around the neck. A U-shaped, semi-circular or mostly circular exterior shell 830 has been carefully fitted (because it is elastic and of similar circumference) around the lateral edges of the face mask 800. Also, the foam rubber nose bridge of the N95, in this embodiment, has been replaced with a nose bridge 825 which is deformable and can conform to the bridge of the nose of a wearer by lightly pressing on the deformable nose bridge 825 to deform it to the shape of the wearers nose. The nose bridge 825 may protect the nose by applying a medical silicone gel (not shown) to the surface of the bridge 825 before placing it on the nose and adjusting its form. Also, the nose bridge 825 may be adapted to clasp the foam rubber nose bridge equipped with the N95 mask interior (see FIGS. 6 and 7) but adapted in size for the individual wearer (who may have a larger nose than most wearers).

Per FIG. 8, a wearer may self-install a cushion of FIG. 5 around the lateral edges of a given face mask that has a lateral edge of a different circumference than a well-known mask such as the N95. A lengthy piece of U-channel or semicircular tubing having A and B ends per FIG. 5 may use a juncture point 835 such as a plug (not shown) to plug one end to the other having cut the cushion of FIG. 5 to fit. One of the A end or B end may be tapered to fit into each other. A wearer would have to cut the cushion to fit cutting the end that is not tapered or for use of a plug or other device to join the ends of the cushion.

Also, per FIGS. 5, 6, 7 and 8, the cushion of the invention may have gel inserted or no gel inserted. Air or water may be used in place of soft gel filler 502, 505. Referring to FIG. 10, air or water or soft gel may be used as the filler of the U-channel opening 1005.

Figure 9:
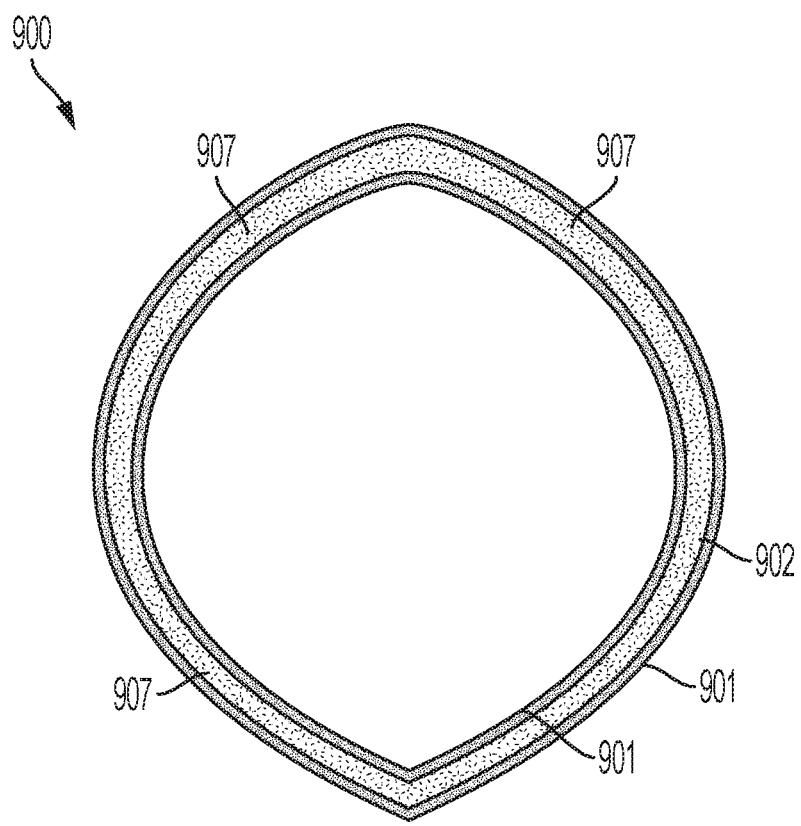
FIG. 9 shows a formed cushion for a face mask having the same or a similar circumference as the lateral edges of an N95 face mask of FIGS. 3 and 4. Component 901 is the clasping shell which clasps the lateral edges of a face mask and component 902 is the interior coating which may coat cloth material and prevent air from escaping from the sides. Reference numeral 907 is intended to represent that the shell 901 and interior coating 902 are continuous and form a predetermined circumference that is elastic medical silicone for protecting the wearer's face and having a coating for preventing against leakage.

FIG. 9 shows a formed soft cushion 900 in a circumferential or somewhat circular shape for a face mask having the same or a similar circumference as the lateral edges of an N95 face mask of FIGS. 3 and 4. Component 901 is the clasping shell which clasps the lateral edges of a face mask and 902 is the interior coating which may be used to make the shell more formable and may be used to coat cloth material and prevent air from escaping from the sides. Component reference numerals 907 are intended to point to a clasped lateral edge of, for example, an N95 or other face mask.

FIG. 10A and FIG. 10B are intended to be considered together where FIG. 10A is a front view of a face mask 1000 and FIG. 10B is a cross-section taken from cylinder 1075 of FIG. 10A which have arrows pointing to cross-section FIG. 10B. The face mask 1000 of FIG. 10A has a circumferential embodiment of a soft U-shaped medical silicone tube-like structure 1030 for clasping the lateral edges of any face mask of similar circumference. The structure 1030 may be manipulated by hand to clasp the lateral edges of a face mask and have an interior 1005 as discussed above. Its exterior may be coated or the lateral edges of the face mask may be wetted with extra soft silicone hardness 0 to 10, petroleum jelly or other soft jelly-like substance to prevent air from leaking from the mask where shell 1030 clasps a face mask lateral edge 1050. Gel or jelly like substance 1005 is seen interior to clasping U-shaped shell 1030 (or air or water may be used as discussed above). FIG. 10B is a cross-section 1075 or a preferred embodiment comprising a clasping shell 1030 for clasping a lateral edge 1050 of a face mask. The same wet extra soft gel or jelly 1005 may be used to coat the interior of the shell 1030 where it clasps the lateral edge 1050.

A method of manufacture of a soft shell cushion apparatus as shown in FIGS. 10A and 10B may comprise injection molding. The apparatus 1030 containing a soft gel or other material (or air) in the length of tubing shown as cross-section 1005 may forming a self-installable fit to a face mask comprising the following steps of manufacture. One first forms a U-shaped channel of predetermined length of medical grade silicone having an extra soft Shore A Hardness scale value between 10 and 40, the predetermined length being measured by measuring a circumference of lateral edges of an N95 face mask. Then the U-shaped channel is filled with medical grade silicone having an extra soft Shore A Harness scale value between 1 and 10, the silicone completely filling the length of U-shaped channel. A final step is using injection molding processes to manufacture a cushion for fitting a particular mask of predetermined lateral edge circumference. In an alternative method, the A and B ends of a shell 1030 may be tapered or fitted together with a plug for sealing A and B ends of the U-shaped channel by joining one end to the other after the filling step. Use of one of heat and bonding material may be applied to the A and B ends (if the shell 1030 is not made in one piece) to join the ends together to comprise a sealed loop.

Other variations of the embodiment of FIG. 10A or 10B may come to mind by careful consideration of the depicted embodiments. Improvements to shape and elasticity may come to mind of one of ordinary skill to fit the cushion apparatus to the plastic of an oxygen or ventilator mask, to a surgical mask or to an N95 face mask to improve comfort and prevent escape of air or oxygen above the nose.

Further, the purpose of the foregoing Abstract is to enable the U.S. Patent and Trademark Office and the public generally and especially the scientists, engineers and practitioners in the relevant art(s) who are not familiar with patent or legal terms or phraseology, to determine quickly from a cursory inspection the nature and essence of this technical disclosure. The Abstract is not intended to be limiting as to the scope of the present invention in any way which should be limited only by the claims which follows.

What is claimed is:

1. A soft shell cushion apparatus for use with a face mask comprising:
    said face mask having a predetermined circumference and lateral edges;
    said soft shell cushion apparatus configured to clasp said lateral edges of said face mask, being detachable and re-useable;
    said soft shell cushion apparatus comprising:
    a soft medical silicone cushion shell formed into one of a U-shape, a semicircular shape and a circular shape, the one shape having a predetermined border shape and predetermined interior shape configured to fit and clasp said lateral edges of said face mask;
    the one shape containing a softer silicone gel filler, said softer silicone gel filler serving to fill said soft medical silicone cushion shell, and
    said softer silicone gel for filling said soft medical cushion shell such that said gel filler contacts the lateral edges of the face mask, promoting comfort to a wearer of the face mask and preventing the lateral edges of the face mask from leaking air to an exterior of the face mask.

2. The soft shell cushion apparatus containing the softer silicone gel filler as recited in claim 1, the soft shell cushion apparatus comprising silicone gel filler having a Shore A hardness value between a value of 0 and 10.

3. The soft shell cushion apparatus containing the softer silicone gel filler as recited in claim 1, the soft medical soft medical silicone cushion shell comprising silicone having a Shore A hardness value between 10 and 40.

4. The soft shell cushion apparatus containing the soft gel as recited in claim 1, the apparatus adapted for use with an N95 face mask having a predetermined cloth material lateral edge of predetermined border shape, the apparatus further comprising:
    a nose bridge for attachment to a foam rubber nose bridge of an N95 mask, the nose bridge comprising the soft medical silicone cushion shell formed into one of a U-shape, a semicircular shape and a circular shape adapted to clasp to the foam rubber nose bridge of the N95 mask, the nose bridge for attachment to the foam rubber nose bridge being of predetermined length and deformable material to be deformed to protect the bridge of a nose of a wearer of the mask and adapted to be coated with a soft silicone gel or a petroleum jelly to prevent the escape of air to reach above the nose and to protect the nose from abrasion.

5. The soft shell cushion apparatus containing the softer silicone gel filler as recited in claim 4, the apparatus being adapted for self-installation by a wearer of the device to clasp the lateral edges of an N95 face mask.

6. A method of manufacture of a soft shell cushion for forming an installable fit to a face mask comprising the steps of:
    measuring a length of a lateral edge surrounding a given face mask,
    forming a U-shaped channel of the measured length of medical grade silicone having an extra soft Shore A Hardness scale value between 10 and 40, the predetermined length being determined by measuring a border shape of the lateral edges of a face mask using injection molding,
    a forming a compartment of the measured length, the compartment for containing soft gel,
    filling the U-shaped channel with a second softer medical grade silicon filler having a second softer Shore A a Harness scale value between 1 and 10, completely filling the measured length of U-shaped channel, and
    using one of a tapered end of the U-shaped channel of the measured length, a plug, heat and a bonding material for fitting two ends of the U-shaped channel of the measured length together by joining one end to the other after the filling to join the ends of the U-shaped channel together to comprise a sealed loop for installation to the face mask.

* * * * *